(12) United States Patent
Speelmans et al.

(10) Patent No.: US 8,076,313 B2
(45) Date of Patent: Dec. 13, 2011

(54) COMPOSITION CONTAINING FERMENTABLE POLYSACCHARIDES

(75) Inventors: Gelske Speelmans, Wageningen (NL); Maria Johanna Adriana Petronella Govers, Bennekom (NL)

(73) Assignee: N.V. Nutricia, Zoetermeer (NL)

( * ) Notice: Subject to any disclaimer, the term of this patent is extended or adjusted under 35 U.S.C. 154(b) by 1055 days.

(21) Appl. No.: 11/574,120

(22) PCT Filed: Aug. 24, 2005

(86) PCT No.: PCT/NL2005/000613
§ 371 (c)(1),
(2), (4) Date: Aug. 27, 2007

(87) PCT Pub. No.: WO2006/022544
PCT Pub. Date: Mar. 2, 2006

(65) Prior Publication Data
US 2008/0280852 A1  Nov. 13, 2008

(30) Foreign Application Priority Data

Aug. 24, 2004  (EP) .................................... 04077393

(51) Int. Cl.
*A61K 31/715* (2006.01)
*A61K 31/736* (2006.01)
(52) U.S. Cl. ........................ 514/54; 514/23; 536/123.1
(58) Field of Classification Search .................. 514/54, 514/23; 536/123.1
See application file for complete search history.

(56) References Cited

U.S. PATENT DOCUMENTS

| 5,827,526 | A | 10/1998 | Dohnalek et al. |
| 6,248,390 | B1 | 6/2001 | Stillman |
| 2004/0131659 | A1 | 7/2004 | Gibson et al. |

FOREIGN PATENT DOCUMENTS

| WO | WO 2004/026294 A1 | 4/2004 |
| WO | WO 2004026294 A1 * | 4/2004 |

OTHER PUBLICATIONS

Alam et al., "Partially hydrolyzed guar gum-supplemented oral rehydration solution in the treatment of acute diarrhea in children," JPGN, vol. 31, No. 5, Nov. 2000, pp. 503-507.
Tuohy et al., "The prebiotic effects of biscuits containing partially hydrolysed guar gum and fructo-oligosaccharides: A human volunteer study," British Journal of Nutrition, vol. 86, No. 3, Sep. 2001, pp. 341-348.

* cited by examiner

*Primary Examiner* — Shaojia Anna Jiang
*Assistant Examiner* — Michael C Henry
(74) *Attorney, Agent, or Firm* — Gilberto M. Villacorta; Sunit Talapatra; Foley & Lardner LLP

(57) ABSTRACT

The present invention relates to a composition to a nutritional composition comprising 0.1 to 15 gram fermentable e partially hydrolysed gum having a degree of polymerization between 10 and 300 per 100 gram dry weight of the composition and 0.1 to 15 gram fermentable, indigestible polysaccharide other than a hydrolysed gum having a DP between 10 and 300 per 100 gram dry weight of the composition.

16 Claims, 1 Drawing Sheet

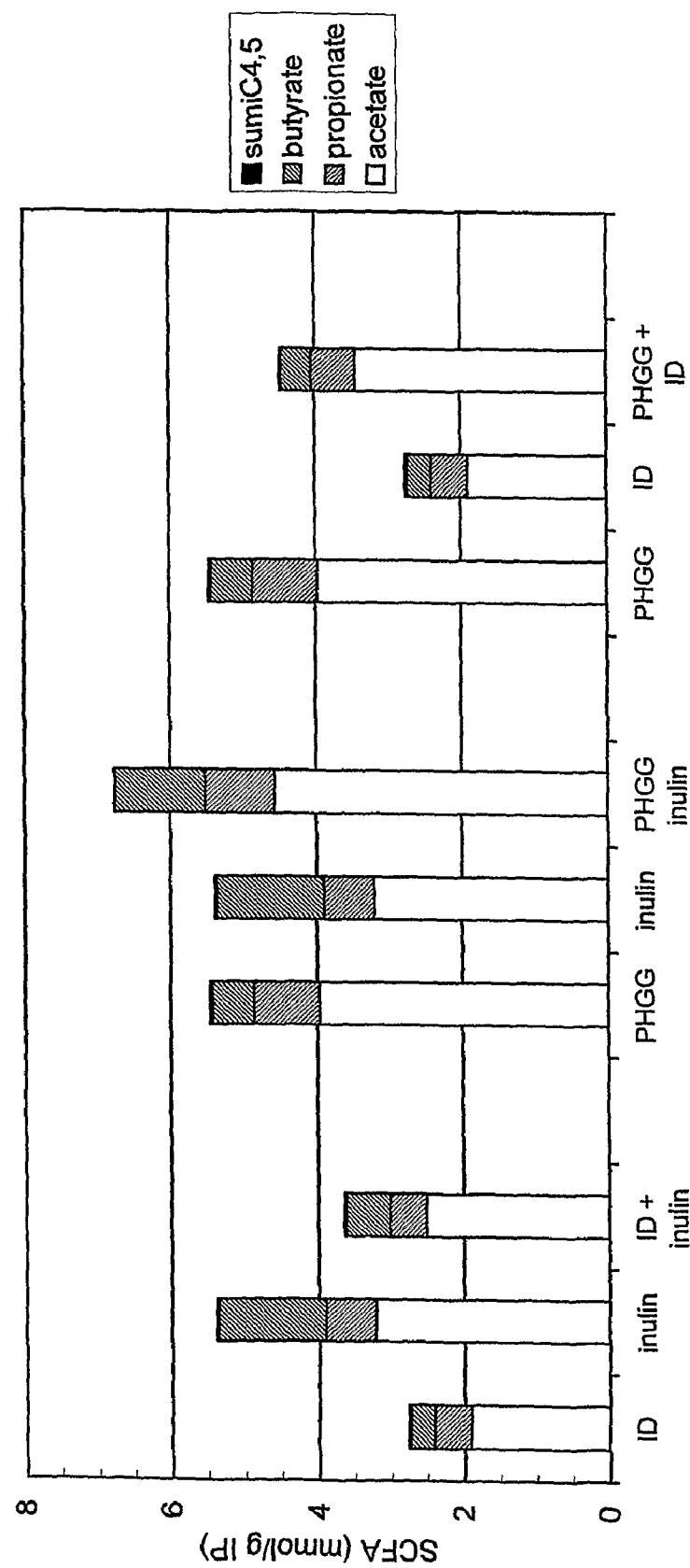

COMPOSITION CONTAINING FERMENTABLE POLYSACCHARIDES

FIELD OF THE INVENTION

The present invention relates to nutritional formula for infants comprising synergistic mixtures of prebiotic polysaccharides and nutritional compositions comprising mixtures of polysaccharides.

BACKGROUND OF THE INVENTION

The microflora of the human large intestine plays a crucial role in human health. The microflora can be modulated by dietary intake. Undigested carbohydrates and undigested proteins are metabolised by the bacteria and as a major end-product of metabolism short-chain fatty acids (SCFA), such as acetate, propionate, butyrate and valerate, are formed, which can subsequently be used by the host. Other examples of end products of bacterial fermentation are lactate and gas.

*Lactobacilli* produce either lactate or lactate plus acetate. *Bifidobacteria* produce lactate and acetate. Fermentation of carbohydrates by *Bifidobacteria, Lactobacilli* and other lactic acid bacteria usually does not lead to the production of propionate, butyrate, isobutyrate, valerate and isovalerate. These SCFA's are indicative of the fermentation of carbohydrates by other bacterial species, such as *Clostridia Bacteroides* or *Enterobacteriaea*, or are indicative for the fermentation of proteins. Therefore, a (relative) increase of intestinal lactate and acetate concomitant with a (relative) decrease of other SCFA's indicates specific stimulation of lactic acid bacteria and/or *Bifidobacteria*.

Mothers' milk appears also to have a bifidogenic effect, as the dominant bacteria that become established in breast-fed infants are *Bifidobacteria*. In contrast, bacterial colonization of infant formula fed infants is not or less dominated by *Bifidobacteria* and is more diverse in bacterial species (Harmsen et al. 2000, J Pediatr Gastroenterol Nutr 30, 61-67). It is thought that non-digestible saccharides present in human milk are responsible for this bifidogenic effect. In the colon and faeces of breast-fed infants the predominant SCFA found is acetate. Furthermore high concentrations of lactate are found.

Several compositions have been proposed in an attempt to mimic the SCFA production profile of breast fed infants. Combinations of small, indigestible oligosaccharides or combinations of small, indigestible oligosaccharides with indigestible polysaccharides such as described in WO0008948 have been proposed. However, a main disadvantage of the use of small, prebiotic oligosaccharides is that it significantly increases the osmotic load in the intestine, which may result in deleterious laxative effects or even worse, diarrhoea.

Using indigestible, polysaccharides with a high molecular weight or a high degree of polymerisation (DP) has the disadvantage that the viscosity of the product is increased. Furthermore, large polysaccharides, with a DP of above 300, are more difficult to ferment by lactic acid bacteria and *Bifidobacteria*.

Therefore, there is a need for nutritional formula comprising prebiotics composed of relatively large, indigestible polysaccharides, which have the desired effect on short chain fatty acid production in the intestine and which does not excessively increase intestinal osmotic load and/or product viscosity.

SUMMARY OF THE INVENTION

The present inventors surprisingly found that the administration of partially hydrolysed guar gum (PHGG) in combination with inulin or indigestible polydextrins, provides a number of synergistic beneficial effects. These effects resemble the effects of combinations of small, indigestible oligosaccharides, however without the undesirable increased intestinal osmotic load and/or product viscosity.

Combinations of inulin and partially hydrolysed guar are known in the art e.g. from WO2004026294. Also Resource® Support™, which is a nutritional liquid product for cancer patients, contains inulin and Benefiber®. However, until now it has not been recognized that this combination of indigestible polysaccharides provides beneficial short chain fatty acid profiles, making them particularly suitable for use in infant nutrition.

The beneficial effects found were significantly more pronounced upon co-administration of a polysaccharide with PHGG than when the single components or when combinations of e.g. inulin and indigestible polysaccharides. This shows that partially hydrolysed polygalactomannan with fructopolysaccharide or partially hydrolysed polygalactomannan with indigestible polydextrin act synergistically. It is further believed that these results are indicative for the synergistic action of infant nutrition comprising partially hydrolysed gum and a second fermentable, indigestible polysaccharide with a DP between 10 and 300 other than hydrolysed gum.

In particular, it was unexpectedly found that fermentation of the present mixture results in a) a synergistic increase in the total amount of SCFA formed; b) a synergistic increase in the total amount of lactate formed; c) an increase in the relative amounts of acetate and lactate; d) a decrease in the relative amounts of butyrate, valerate and branched short chain fatty acids; and/or e) a decreased amount of gas formed per mmol SCFA.

Inclusion of the present combination of indigestible polysaccharides in an infant nutrition thus results in a composition, which highly resembles the effects of mothers' milk. Hence, in one embodiment the invention provides the use of a combination of partially hydrolysed galactomannan and a polysaccharide selected from fructopolysaccharide or indigestible polydextrin, for the preparation of compositions which lead to a colonic environment essentially similar to that of breast-fed infants is.

Administration of the present composition therefore can be used to achieve one or more of the following physiological effects: a significant increase of *Bifidobacteria* and/or lactic acid bacteria; a significant increase in lactic acid and/or a significant increase in total SCFA; a significant increase in relative amount of acetate; a significant decrease in relative amount of butyrate; a significant decrease in the sum of isobutyrate, valerate and isovalerate; a decreased formation of gas; a longer and more even fermentation, including fermentation in the most distal parts of the colon, and a high fermentation in the most proximal part of the colon.

Through these changes in lactic acid bacteria, *Bifidobacteria*, lactate levels, SCFA levels and profile, the composition provides one or more of the following effects:

Reduced intestinal permeability at the site of SCFA production. This is important for preventing disease and maintaining health, especially to prevent allergies from developing.

Decreased occurrence of spontaneous contractions and the colonic muscle tension resulting in less cramps, less colics and less abdominal pain.

Increased calcium-ion absorption, which is important for bone mineralisation and bone development.

Increased mucus production of the intestinal mucosa, which provides protection against pathogen attachment and colonization.

Lowered pH resulting in inhibition of pathogenic bacteria.

This novel synergistic interaction of partially hydrolysed galactomannan and other indigestible polysaccharides on the formation of SCFA and lactate leads to new uses in the treatment or prevention of diarrhea, colic and/or abdominal cramps and allergy.

The present nutritional compositions comprising these prebiotic mixtures can also be used for adults having intestinal problems such as inflammatory bowel disease (IBD) or irritable bowel syndrome (IBS).

DETAILED DESCRIPTION OF PREFERRED EMBODIMENTS

The present invention provides a method for providing nutrition to an infant, said method comprising administering the nutritional composition to an infant, characterised in that the composition comprises:
indigestible, fermentable, partially hydrolysed gum having a degree of polymerisation (DP) between 10 and 300 in an amount of 0.1 to 15 grams per 100 g dry weight of said nutritional composition; and
indigestible, fermentable, soluble polysaccharide having a degree of polymerisation (DP) between 10 and 300, other than partially hydrolysed gum, in an amount of 0.1 to 15 gram per 100 g dry weight of said nutritional composition.

The present invention also provides a composition comprising 5 to 16 en % protein, 35 to 60 en % fat; and 25 to 75 en % carbohydrates, comprising:
0.1 to 15 gram indigestible, fermentable, partially hydrolysed gum having a degree of polymerisation (DP) between 10 and 300 per 100 gram dry weight of the composition; and
0.1 to 15 gram indigestible, fermentable, soluble polysaccharide having a DP between 10 and 300 per 100 gram dry weight of the composition other than partially hydrolysed gum.

With degree of polymerisation (DP) as used herein is meant number of monomer units joined together in the poly- or oligomer.

The term "soluble" as used herein, when having reference to a polysaccharide, fibre or oligosaccharide, means that the substance is at least 50% soluble according to the method described by L. Prosky et al., J. Assoc. Off. Anal. Chem. 71, 1017-1023 (1988).

The term "fermentable" as used herein refers to the capability to undergo (anaerobic) breakdown by microorganisms in colon to smaller molecules, in particular short chain fatty acids and lactate. The fermentability may be determined e.g. by the method described in Am. J. Clin. Nutr. 53, 1418-1424 (1991).

Gum

The present composition comprises 0.1 to 15 gram indigestible, fermentable, partially hydrolysed gum having a degree of polymerisation (DP) between 10 and 300, per 100 grain dry weight of the composition. The hydrolysed gum is preferably water-soluble. The term "partially hydrolysed" as used herein refers to a composition which has been subjected to hydrolyses (e.g. heat, mechanic, acid or enzymatic) and has not been hydrolysed to its monosaccharide units.

The term "gum" as used herein refers to refers to the commonly available natural gums and more particularly to konjac gum, xanthan gum, guar gum (guaran gum), locust (carob) bean gum, tara bean gum, gum tragacanth, arabic gum or gum acacia, karaya gum, gum ghatti, algin gum, talha gum, gellan gum, and other gums.

In one embodiment of the invention, preferably indigestible, fermentable, partially hydrolysed galactomannan is used. Galactomannan consists of β-(1,4)-D-mannopyrasyl units in the main, linear chain, and galactose branches bound thereto via α-(1,4)-D bonds. According to a particularly preferred embodiment guar gum, locust bean gum and/or tara gum are used.

Partially hydrolysed galactomannan may be obtained partial or limited hydrolysis. The galactomannan gum molecules are reduced in size by an enzyme, such as a β-mannase, or/and by a chemical/physical treatment. By this treatment not only the viscosity is lowered to values below 20 cps of a 10% solution in water at 25° C. as determined by a Brookfield viscometer.

According to a particularly preferred embodiment, partially hydrolysed guar gum (PHGG) is used. Guar gum is a polysaccharide obtainable from the endosperm of *Cyamopsis tetragonolobus* and contains mainly high molecular weight hydrocolloidal polysaccharide, composed of galactose and mannose units combined through glycosidic linkages. Specifically, the guar gum preferably consists of linear chains of (1→4) beta-D-mannopyranosyl units with alpha-D-galactopyranosyl units attached by (1→6) linkages. PHGG is commercially available under the tradename Benefiber® from Novartis Nutrition Corporation or under the tradename "Sunfiber AG®" from Taiyo Kagaku, Japan. Preferably, the hydrolysed gum is in an agglomerated form, which has better solubility.

The present composition preferably comprises between 0.5 and 8 grams, even more preferably between 1 and 5 grams indigestible, fermentable, partially hydrolysed gum having a degree of polymerisation (DP) between 10 and 300 per 100 gram dry weight, particularly PHGG. Preferably these amounts of indigestible, fermentable, partially hydrolysed gum are provided by indigestible, fermentable, partially hydrolysed gum having a degree of polymerisation (DP) between 20 and 150, even more preferably between 25 and 100.

Polysaccharide

The present invention comprises indigestible, fermentable, soluble polysaccharide with a DP between 10 and 300 other than partially hydrolysed gum, in an amount of between 0.1 and 15 grams per 100 gram dry weight of the composition. Said indigestible, fermentable, soluble polysaccharide is preferably selected from the group consisting of fructopolysaccharide and indigestible polydextrin.

The present composition preferably comprises between 0.5 and 8 grams, even more preferably between 1 and 5 grams indigestible, fermentable, polysaccharide.

The term "fructopolysaccharide" refers to a polysaccharide carbohydrate comprising a chain of at least 10 β-linked fructose units with a DP between 10 and 300, preferably between 20 and 300. Preferably inulin is used. Inulin is available under the tradename "Raftilin HP®", (Orafti). The term "inulin" is used herein to refer to glucose-terminated fructose chains with at least 90% fructose units having a DP between 10 and 300. Inulin can be described as $GF_n$, wherein G represents a glucosyl unit, F represents a fructosyl unit and n is the number of fructosyl units linked to each other, n being 9 or more. A small part of the inulin molecules, however, may have no terminal glucose unit, due to hydrolysis during processing. The average DP of the fructopolysaccharide is preferably at least 15, more preferably at least 20 or more, up to 300. In inulin the fructose units are linked with a β(2→1) linkage.

The present composition preferably comprises between 0.5 and 8 grams, even more preferably between 1 and 5 grams fructopolysaccharides.

Indigestible polydextrins refer to digestion-resistant (malto)dextrins or digestion-resistant polydextrose which have a DP of 10 to 50, preferably between 10 and 20. Indigestible polydextrins are at least 75% indigestible, preferably at least 90% indigestible These indigestible polydextrins are preferably produced by a combination of hydrolysis and transglucosidation reactions. In a preferred embodiment, the indigestible polydextrins comprise $\alpha(1\rightarrow 4)$, $\alpha(1\rightarrow 6)$ glucosidic bonds and $1\rightarrow 2$ and $1\rightarrow 3$ linkages Indigestible polydextrins are for example available under the tradename "Fibersol 2®" from Matsutami Inductries or Litesse® from Danisco.

The present composition preferably comprises between 0.5 and 8 grams, even more preferably between 1 and 5 grams indigestible polydextrin.

Ratio

The present composition preferably has a weight ratio indigestible, fermentable, polysaccharide:indigestible, fermentable, partially hydrolysed gum ranging from 1:19 to 19:1, preferably 1:4 to 4:1, more preferably 0.5:1 to 2:1. The synergistic effect of the two indigestible polysaccharides will become more and more evident, when the ratio of the two indigestible polysaccharides approaches 1:1.

Liquid Composition

The present composition is preferably administered in liquid form. In order to meet the caloric requirements, the composition preferably contains 50 to 200 kcal/100 ml, more preferably 60 to 90 kcal/100 ml. The osmolarity of the present composition is typically between 150 and 420 mOsmol/l, preferably 260 to 320 mOsmol/l. The low osmolarity aims to reduce the gastrointestinal stress, e.g. reduce the incidence of diarrhea, particularly in infants.

Preferably the composition is in a liquid form, with a viscosity below 35 cps. When suitable, the composition is in a powdered from, which can be reconstituted with water to from a liquid.

Daily Dosages

When the composition is a liquid form, the preferred volume administered on a daily basis is in the range of about 80 to 2500 ml, more preferably about 450 to 1000 ml per day, which is a suitable amount for an infant. An infant is a human of 0 to 36 months of age.

A daily effective dose of the present composition preferably comprises 1 to 40 g fermentable, indigestible polysaccharide/day, including hydrolysed gum and soluble, fermentable, indigestible polysaccharide, preferably 2 to 10 g/day. The concentration of the sum of a) partially hydrolysed gum (preferably PHGG) and b) soluble, indigestible polysaccharide preferably selected from the group consisting of fructopolysaccharide or indigestible polydextrin, is preferably 0.2 to 5 g/100 ml, more preferably between 0.2 and 3.5 g/100 ml, even more preferably between 0.3 to 2.4, and most preferably between 0.35 to 1.0 gram per 100 ml.

Treatment

The present composition can advantageously be used in a method for the treatment and/or prevention of diarrhea, (gastrointestinal) infections, colics, abdominal cramps, abdominal pain, irritable bowel syndrome (IBS), inflammatory bowel disease (IBD), allergy, eczema, asthma and/or atopic diseases. In a preferred embodiment, the present invention is used in a method for the treatment or prevention of allergy or allergic reactions.

The present composition is preferably administered orally. The composition is particularly useful in a method for providing nutrients to an infant and/or stimulating the growth of an infant. As the composition is particularly useful for stimulating the maturation of the intestinal flora, the composition is advantageously administered to an infant of 0-6 years preferably to an infant of 0-48 months, more preferably to an infant of 0-18 months, even more preferably to an infant 0-12 months. The younger an infant is, the more important a lactic acid bacteria dominated intestinal flora is.

Macronutrients

The present composition contains 5 to 16 en % protein; 35 to 60 en % fat; and 25 to 75 en % carbohydrates, preferably 5 to 12.0 en % protein; 39 to 50 en % fat; and 40 to 55 en % carbohydrates (en % is short for energy percentage and represents the relative amount each constituent contributes to the total caloric value of the preparation).

The composition preferably contains 1.4 to 6 g of a protein source per 100 ml. The composition comparably contains 8.5 to 19 g per 100 g dry weight. The protein source may comprise large, intact protein, hydrolysed proteins, peptides or free amino acids or mixtures thereof. Suitable protein sources are cow's milk protein, casein, whey and soy protein. The protein content is based on the Kjeldahl percentage, N*6.38. The composition preferably further contains 2.1 to 6.5 g fat per 100 ml, containing 0.3 to 1.5 g linoleic acid (LA) per 100 mil, at least 50 mg α-linolenic acid (ALA) per 100 ml, in which the ratio of LA/ALA ranges from of 5 to 15. Based on dry weight the composition preferably contains 12.5 to 30 g fat, 1.8 to 12.0 g LA, and at least 0.30 g ALA per 100 g, in which the ratio of LA/ALA ranges from 5 to 15. The amount of saturated fatty acids is preferably between 10 and 58 wt. % of total fatty acids, the concentration of monounsaturated fatty acids ranges from 17 to 60% based on weight of total fatty acids and the concentration of polyunsaturated fatty acids ranges from 11 to 36% based on weight of total fatty acids. These amounts and ratios of ALA and LA have the advantage that a balanced biosynthesis of n-3 and n-6 polyunsaturated fatty acids is achieved. Preferably the present composition contains long chain polyunsaturated fatty acids (LC PUFA), such as eicosapentaenoic acid (EPA), docosahexaenoic acid (DHA) and arachidonic acid (AA). Suitable lipid sources are milk fats, canola oil, safflower oil, sunflower oil, olive oil, coconut oil, marine oils, etc. or fractions or mixtures thereof comprising suitable fatty acids.

The present composition preferably contains 6 to 19 g digestible carbohydrates per 100 ml, preferably 6-19 gram lactose. Other suitable sources of digestible carbohydrates are maltodextrin, starch, sucrose, glucose, and maltose.

Probiotics

According to an even further preferred embodiment the present composition contains probiotic bacteria. Probiotic bacteria are live microbial food ingredients that have a beneficial effect on human health. Probiotic bacteria most commonly are "lactic acid bacteria", so-called because lactic acid is a major product formed upon fermentation of carbohydrates. The present composition preferably contains members of the genera *Lactobacillus* and/or *Bifidobacterium*. *Bifidobacteria* and *Lactobacilli* are bacteria which are especially present in the colon of breast-fed infants. The presence of probiotics further enhances the fermentation of the polysaccharide mixture into SCFA (especially acetate) and lactate in the colon, thereby further enhancing the generation of a healthy colonic environment, especially for infants. The concentration of probiotics preferably is $1*10^7$ colony forming units (cfu) to $2*10^{10}$ cfu per 100 ml, preferably $1*10^8$ cfu to $2*10^9$ cfu per 100 ml. Based on dry weight the concentration is preferably between $6*10^7$ and $1*10^{11}$ cfu/100 g, preferably between $6*10^8$ and $3*10^{10}$ cfu/100 g

LEGEND TO THE FIGURE

FIGURE: Formation of short chain fatty acids in mmol/g indigestible polysaccharide (IP) after 48 h in vitro fermentation of partially hydrolysed guar gum (PHGG); inulin; indigestible polydextrin (ID); a mixture of partially hydrolysed guar gum and inulin (weight ratio 1:1); a mixture of partially hydrolysed guar gum and indigestible polydextrin (weight ratio 1/1) and a mixture of inulin and indigestible polydextrin by fresh faeces obtained from babies. Sum iC4,5 is the sum of valerate, isobutyrate and isovalerate. The data were corrected for blanc fermentation. The FIGURE shows that a combination PHGG and inulin or indigestible polydextrin synergistically improve SCFA formation. The results are indicative for the advantageous use of these combinations in baby foods.

EXAMPLES

Example 1

Synergistic Effects on Fermentation Patterns

Materials:
Microflora was obtained from fresh faeces from babies fed with infant formula. Fresh faecal material from three bottle-fed babies ranging 6 to 12 months of age was pooled and put into preservative medium within 2 h.

Preservative medium: Buffered peptone 20.0 g/l, L-Cysteine-HCl 0.5 g/l, Sodium thioglycollate 0.5 g/l, resazurine tablet 1 per liter, adjust to pH 6.7±0.1 with 1 M NaOH or HCl. Boil in microwave. Fill 30 ml serum bottles with 25 ml medium. Sterilise 15 minutes at 121° C.

McBain & MacFarlane medium: Buffered peptone water 3.0 g/l, yeast extract 2.5 g/l. mucin (brush borders) 0.8 g/l, tryptone 3.0 g/l, L-Cysteine-HCl 0.4 g/l, bile salts 0.05 g/l, $K_2HPO_4.3H_2O$ 2.6 g/l, $NaHCO_3$ 0.2 g/l, NaCl 4.5 g/l, $MgSO_4.7H_2O$ 0.5 g/l, $CaCl_2$ 0.228 g/l, $FeSO_4.7H_2O$ 0.005 g/l. Fill 500 ml Scott bottles with the medium and sterilise 15 minutes at 121° C.

Buffered medium: $K_2HPO_4.3H_2O$ 2.6 g/l, $NaHCO_3$ 0.2 g/l, NaCl 4.5 g/l, $MgSO_4.7H_2O$, 0.5 g/l, $CaCl_2$ 0.228 g/l, $FeSO_4.7H_2O$ 0.005 g/l. Adjust to pH 6.3±0.1 with $K_2HPO_4$ or $NaHCO_3$. Fill 500 ml Scott bottles with the medium and sterilise 15 minutes at 121° C.

Faecal suspension: The preserved solution of faeces is centrifuged at 13,000 rpm for 15 minutes. The supernatant is removed and the faeces is mixed with the McBain & Mac Farlane medium in a weight ratio of 1:5.

Partially hydrolysed guar gum used was SunFiber® obtained from Taiyo. Indigestible polydextrin used was Fibersol-2® obtained from Matsutani. Fructopolysaccharide used was RaftilineHP® obtained from Orafti.

Methods:
The fresh baby faeces were mixed with the preservative medium within 2 h and stored at 4° C. for 0-3 h. The fermentation experiments were started within 3 h of storage.

Fermentation: 15.0 ml of the faecal suspension was combined with a) 500 mg SunFiber, b) 500 mg Fibersol-2, c) 500 mg RaftlineHP, d) 250 mg SunFiber+250 mg RaftlineHP, e) 250 mg SunFiber+250 mg Fibersol-2, f) 250 mg RaftlineHP+250 mg Fibersol-2 or g) with no addition (Blanc), and mixed thoroughly in a bottle. A t=0 sample was withdrawn (0.5 ml). 14.5 ml of the resulting suspension was brought in a dialysis tube in a 250 ml bottle filled with 250 ml of the buffered medium. The bottle was closed well and incubated at 37° C. Samples were taken from the dialysis tube (0.5 ml) or from the dialysis buffer (1.0 ml) with a hypodermic syringe after 3, 24, and 48 hours and immediately put on ice to stop fermentation. The samples were subsequently stored at −20° C.

Analysis SCFA: The samples were thawed in icewater, diluted 10× in MilliQ. 350 µl sample was mixed with 200 µl 5% (v/v) formic acid, 100 µl 1.25 g/l 2-ethylbutyric acid (Sigma-Aldrich, Zwijndrecht, The Netherlands) and 350 µl MilliQ. Acetic, propionic, n-butyric, iso-butyric and n-valeric acids were quantitatively determined by a Varian 3800 gas chromatograph (GC) (Varian, Inc., Walnut Creek, U.S.A.) equipped with a flame ionisation detector. 0.5 µl of the sample was injected at 80° C. in the column (Stabilwax, 15 m×0.53 mm, film thickness 1.00 µm, Restek Co., USA) using helium as carrier gas (3.0 psi). New columns were conditioned overnight at 200° C. After injection of the sample, the oven was heated to 160° C. at a speed of 16° C./min, followed by heating to 220° C. at a speed of 20° C./min and finally maintained at a temperature of 220° C. for 1.5 minutes. The temperature of the injector and the detector was 200° C. After every ten samples the column was cleared by injection of 0.5 µl 1% (v/v) formic acid to avoid memory effects of the column, followed by injection of 0.5 µl standard SCFA mix (1.77 mM acetic acid, 1.15 mM propionic acid, 0.72 mM n-butyric acid, 0.72 mM iso-butyric acid, 0.62 mM n-valeric acid obtained from Sigma-Aldrich, Zwijndrecht, The Netherlands) to monitor the occurrence of memory effects. The levels of SCFA were determined using 2-ethylbutyric acid as an internal standard.

Analysis lactic acid: Samples were thawed on ice and centrifuged for 5 minutes at 14,000 rpm. 100 µl supernatant was heated for 10 minutes at 100° C. to inactivate all enzymes. Concentrations of L-lactic acid and D-lactic acid were determined enzymatically using a L-lactic acid detection kit and D-lactate-dehydrogenase (Boehringer Mannheim, Mannheim, Germany).

Results:
Results are shown in the FIGURE. The FIGURE shows that use of a mixture of PHGG and inulin surprisingly resulted in a significantly higher amount of SCFA, especially acetate, formed per g indigestible polysaccharide compared to the single components or when the additive effect of the single components was taken into account. The additive effect is the average of the fermentation results calculated from the results of the fermentation with RaftilinHP only and with SunFiber only. These results show the synergistic effect of PHGG and inulin, and are indicative for the synergistic effect of the present composition in (infant) nutrition.

Fermentation of the mixture of PHGG and inulin shows a significantly lower amount and percentage of isobutyrate plus isovalerate plus valerate than when the single components were fermented (PHGG 0.029, inulin 0.021, PHGG+inulin: 0.010 mmol/g indigestible polysaccharide).

Fermentation of a mixture of PHGG with indigestible polydextrin surprisingly resulted in a higher amount of SCFA, especially acetate, which exceeded the theoretical additive effect of the two indigestible polysaccharides. Fermentation of a mixture of PHGG and indigestible polydextrin results in a synergistically increased amount of acetate, while the amount of butyrate was decreased and the (relative) amount of isobutyrate plus isovalerate plus valerate was decreased (PHGG 0.029, ID 0.028, PHGG+ID 0.017 mmol/g indigestible polysaccharide).

Unexpectedly, fermentation of the combination of indigestible polydextrin and inulin did not provide the synergistic increase in SCFA production, but showed a reduced SCFA production. It also resulted in higher relative amounts of isobutyrate plus isovalerate plus valerate.

After 3 h in vitro fermentation by infant faeces lactate production was determined. Table 1 shows the metabolic end-products formed at that time point. A synergistically increased formation of lactate is observed for the mixture PHGG with inulin or indigestible polydextrin. A combination of inulin and indigestible polydextrin does not show such an effect.

TABLE 1

| Testcomponent | Lactate (μmol/g indigestible polysaccharide) |
|---|---|
| SunFiber | 5 |
| RaftilinHP | 0 |
| Fibersol-2 | 68 |
| SunFiber + Fibersol-2 | 89 |
| SunFiber + RaftilinHP | 24 |
| Fibersol-2 + RaftlinHP | 44 |

Kinetics of SCFA Formation

Table 2 shows the kinetics of SCFA formation in mmol/g indigestible polysaccharide (blanc corrected) (% of total SCFA formed in 48 h). The combination of PHGG with inulin still shows a high SCFA formation between 24 and 48 h, indicating that in the distal part of the colon still SCFA is formed. Yet, also in the first 3 h a high amount of SCFA is formed.

The mixture of PHGG+indigestible polydextrin also results in an increased formation of SCFA during the last 24 h and during the first 3 h. These effects are synergistic; they are larger than the additive effects of the single components.

TABLE 2

| | Time interval (hours) | | |
|---|---|---|---|
| | 0-3 hrs | 3-24 hrs | 24-48 hrs |
| SunFiber | 0.41 (8%) | 3.92 (78%) | 0.68 (14%) |
| RaftilinHP | 0.21 (4%) | 4.04 (82%) | 0.70 (14%) |
| Fibersol-2 | 0.42 (18%) | 1.42 (61%) | 0.50 (21%) |
| SunFiber + Fibersol-2 | 0.57 (14%) | 2.67 (67%) | 0.76 (19%) |
| SunFiber + RaftilinHP | 0.34 (5%) | 4.15 (66%) | 1.84 (29%) |

The following examples are non-limiting examples of compositions containing synergistic mixtures of fermentable polysaccharides.

Example 2

A liquid composition, which is formed after reconstituting 13.5 g powder with water to a final volume of 100 ml, containing per final 100 ml:

| | | |
|---|---|---|
| Energy: | 67 | kcal |
| Protein: | 8 | en % |
| | 1.4 | g |
| | 0.6 | g casein |
| | 0.8 | g whey |
| Digestible Carbohydrates: | 45 | en % |
| | 7.5 | g |
| | 7.3 | g lactose |
| | 0.2 | g other carbohydrates |
| Fat: | 47 | en % |
| | 3.5 | g |
| | 1.5 | g saturated |
| | 1.5 | g monounsaturated |
| | 0.5 | g polyunsaturated |
| | 0.4 | g linoleic acid |
| | 0.07 | g α-linolenic acid |
| Indigestible polysaccharide | 0.4 | g |
| | 0.1 | g fructopolysaccharide |
| | 0.3 | g partially hydrolysed guar gum |
| Osmolarity: | 300 | mOsmol/l |

The composition further contains minerals, trace elements, vitamins and choline and taurine in amounts in compliance with the international guidelines for infant milk formula.

Example 3

A liquid composition, which is formed after reconstituting 15.8 g powder with water to a final volume of 100 ml, containing per final 100 ml:

| | | |
|---|---|---|
| Energy: | 72 | kcal |
| Protein: | 11 | en % |
| | 1.9 | g (partially hydrolysed whey protein) |
| Digestible Carbohydrates: | 40 | en % |
| | 8.7 | g |
| | 3.9 | g sugars |
| | 3.0 | g lactose |
| | 0.9 | g others |
| | 4.8 | g polysaccharides |
| | 2.0 | g starch |
| | 2.8 | g others |
| Fat: | 40 | en % |
| | 3.3 | g |
| | 1.4 | g saturated (including 1.4 g β-palmitate) |
| | 1.4 | g monounsaturated |
| | 0.5 | g polyunsaturated |
| | 0.43 | g linoleic acid |
| | 0.08 | g α-linolenic acid |
| Indigestible polysaccharide: | 0.8 | g |
| | 0.4 | g indigestible polydextrin |
| | 0.4 | g partially hydrolysed guar gum |
| Probiotics: | 1.5 | $10^8$ colony forming units of Bifidobacteria |
| Osmolarity: | 270 | mOsmol/l |

Example 4

A liquid composition containing:
Per 100 ml:

| | |
|---|---|
| Energy: | 150 kcal |
| Protein: | 9 en % |
| | 3.4 g (casein) |
| Digestible Carbohydrates: | 50 en % |
| | 18.8 g |
| | 3.0 g sucrose |
| | 0.9 g maltose |
| | 14.3 g polysaccharides |
| | 0.6 g others |
| Fat: | 41 en % |
| | 6.8 g 6.9 g ?? |
| | 0.7 g saturated |
| | 4.1 g monounsaturated |
| | 2.0 g polyunsaturated |
| | 1.62 g linoleic acid |
| | 0.34 g α-linolenic acid |
| Indigestible polysaccharide | 1.5 g |
| | 0.8 g fructopolysaccharide |
| | 0.7 g partially hydrolysed guar gum |
| Osmolarity: | 390 mOsmol/l |

The composition further contains minerals, trace elements, vitamins, carnitine, taurine and choline in amounts in compliance with the international recommendations.

The invention claimed is:

1. A method for providing nutrition to an infant comprising administering a nutritional composition to the infant, said composition having a caloric density of 50 to 200 kcal/100 ml and comprising:
   (i) protein, wherein 5 to 16% of the total energy of the composition is derived from the protein,
   (ii) fat, wherein 35 to 60% of the total energy of the composition is derived from the fat;
   (iii) carbohydrates, wherein 25 to 75% of the total energy of the composition is derived from the carbohydrates,
   a) 0.1 to 15 gram indigestible, fermentable, partially hydrolysed gum having a degree of polymerisation (DP) between 10 and 300 per 100 gram dry weight of the composition; and
   b) 0.1 to 15 gram indigestible, fermentable, soluble polysaccharide having a DP between 10 and 300 per 100 gram dry weight of the composition other than partially hydrolysed gum,
   wherein the weight ratio a):b) is between 19:1 and 1:19.

2. The method according to claim 1, wherein the carbohydrate is a digestible carbohydrate.

3. The method according to claim 2, wherein composition comprises 9 to 16 g digestible carbohydrate per 100 ml.

4. The method according to claim 1, wherein the administering provides 1 to 40 g indigestible, fermentable, polysaccharide per daily dose.

5. A composition comprising:
   (i) protein, wherein 5 to 16% of the total energy of the composition is derived from the protein,
   (ii) fat, wherein 35 to 60% of the total energy of the composition is derived from the fat;
   (iii) carbohydrates, wherein 25 to 75% of the total energy of the composition is derived from the carbohydrates,
   a) 0.1 to 15 gram indigestible, fermentable, partially hydrolysed gum having a degree of polymerisation (DP) between 10 and 300 per 100 gram dry weight of the composition; and
   b) 0.1 to 15 gram indigestible, fermentable, soluble polysaccharide having a DP between 10 and 300 per 100 gram dry weight of the composition other than partially hydrolysed gum,
   wherein the weight ratio a):b) is between 19:1 and 1:19.

6. The composition according to claim 5, wherein the partially hydrolysed gum is galactomannan gum or guar gum or both.

7. The composition according to claim 5, wherein the polysaccharide is fructopolysaccharide or polydextrin or both.

8. The composition according to claim 6, wherein the polysaccharide is fructopolysaccharide or polydextrin or both.

9. The composition according to claim 8, wherein the gum is galactomannan gum and the polysaccharide is fructopolysaccharide or polydextrin.

10. The composition according to claim 6, comprising 0.1 to 15 gram of guar gum having a degree of polymerisation (DP) between 10 and 300.

11. The composition according to claim 5, wherein the fat comprises 1.8 to 12.0 g linoleic acid (LA) per 100 g dry weight, at least 0.3 g α-linolenic acid (ALA) per 100 g dry weight, in which the ratio of LA/ALA ranges from of 5 to 15, characterised in that the concentration of saturated fatty acids ranges from 10% to 58% (based on total fatty acids), the concentration of monounsaturated fatty acids ranges from 17 to 60% based on total fatty acids and the concentration of polyunsaturated fatty acids ranges from 11 to 36% based on total fatty acids.

12. The composition according to claim 5 comprising 5 to 12 energy % protein; 39 to 50 energy % fat; and 40 to 55 energy % carbohydrates.

13. The composition according to claim 5 having an osmolarity between 100 and 420 mOsm/1 and a viscosity below 35 cps.

14. The composition according to claim 5, having a caloric density of 50 to 200 kcal/100 ml.

15. A composition comprising:
   (i) protein, wherein 5 to 16% of the total energy of the composition is derived from the protein,
   (ii) fat, wherein 35 to 60% of the total energy of the composition is derived from the fat;
   (iii) carbohydrates, wherein 25 to 75% of the total energy of the composition is derived from the carbohydrates,
   (iv) indigestible carbohydrates comprising:
      (a) 0.1 to 15 gram galactomannan gum; and
      (b) 0.1 to 15 gram fructopolysaccharide or polydextrin,
   wherein the weight ratio (a):(b) is between 19:1 and 1:19.

16. The composition according to claim 15 having an osmolarity between 100 and 420 mOsm/1 and a viscosity below 35 cps.

* * * * *